US012778892B2

(12) United States Patent
Sheikhlary

(10) Patent No.: US 12,778,892 B2
(45) Date of Patent: Nov. 3, 2026

(54) RADIOPROTECTIVE COMPOSITIONS AND METHODS FOR PREPARATION THEREOF

(71) Applicant: ARIZONA BOARD OF REGENTS ON BEHALF OF THE UNIVERSITY OF ARIZONA, Tucson, AZ (US)

(72) Inventor: Sara Sheikhlary, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 176 days.

(21) Appl. No.: 18/939,320

(22) Filed: Nov. 6, 2024

(65) Prior Publication Data

US 2025/0161217 A1 May 22, 2025

Related U.S. Application Data

(60) Provisional application No. 63/600,920, filed on Nov. 20, 2023.

(51) Int. Cl.

| | |
|---|---|
| *A61K 31/352* | (2006.01) |
| *A61K 9/1272* | (2025.01) |
| *A61K 36/16* | (2006.01) |
| *A61K 36/534* | (2006.01) |
| *A61K 47/36* | (2006.01) |
| *A61P 43/00* | (2006.01) |

(52) U.S. Cl.

CPC .......... *A61K 9/1272* (2013.01); *A61K 31/352* (2013.01); *A61K 36/16* (2013.01); *A61K 36/534* (2013.01); *A61K 47/36* (2013.01); *A61P 43/00* (2018.01)

(58) Field of Classification Search

CPC .................................................... A61K 36/534

See application file for complete search history.

(56) References Cited

FOREIGN PATENT DOCUMENTS

CA 2902171 A1 * 8/2014 ............. A61Q 17/00

* cited by examiner

*Primary Examiner* — Benjamin J Packard

(74) *Attorney, Agent, or Firm* — NGUYEN TARBET IP LAW

(57) ABSTRACT

A multi-layer niosome nanocarrier drug composition for optimized drug delivery is described herein. The composition comprises chloroform extract of mint, Kaempferol Iodine-127 in the inner layer, and fulvic acid in the outer layer of the niosome. The method of preparing the composition is also described herein and may involve dissolving components in chloroform and incubating kaempferol-iodine-loaded niosomes in fulvic acid. The process ensures efficient drug release and enhanced therapeutic efficacy.

20 Claims, 2 Drawing Sheets

RADIOPROTECTIVE COMPOSITIONS AND METHODS FOR PREPARATION THEREOF

CROSS-REFERENCE TO RELATED APPLICATIONS

This application is a non-provisional and claims benefit of U.S. Provisional Application No. 63/600,920 filed Nov. 20, 2023, the specification of which is incorporated herein in their entirety by reference.

FIELD OF THE INVENTION

The present invention features radioprotective compositions and methods for preparing said compositions.

BACKGROUND OF THE INVENTION

The escalating prevalence of radiation exposure in various fields, from medical treatments to industrial processes, underscores the imperative for effective radioprotective measures. Exposure to ionizing radiation poses substantial risks to living organisms, with potential consequences ranging from cellular damage to severe health complications. Traditional radioprotective strategies, while essential, often exhibit limitations in terms of efficacy and side effects.

In light of these challenges, the present invention focuses on developing innovative radioprotective drugs designed to provide a robust defense against the adverse effects of ionizing radiation. The present invention aims to enhance protection against radiation-induced damage and mitigate the undesirable side effects associated with existing interventions by leveraging novel drug formulations and molecular approaches. Thus, the present invention compositions and methods for safeguarding individuals exposed to ionizing radiation across various contexts, from medical diagnostics and treatments to unforeseen radiological events.

BRIEF SUMMARY OF THE INVENTION

It is an objective of the present invention to provide compositions and methods that allow for radioprotection, as specified in the independent claims. Embodiments of the invention are given in the dependent claims. Embodiments of the present invention can be freely combined with each other if they are not mutually exclusive.

The present invention may feature a composition called "Herbostroiodine," which is an herbal extended-release radio-protective drug formulated using a multi-layer niosome nanocarrier. In some embodiments, the composition described herein comprises about 5 to 15 mg chloroform extract of Mint (*Mentha arvensis* Linn), about 15 to 25 mg Kaempferol Iodine-127 (non-radioactive iodine isotope conjugated with Kaempferol) in the inner layer of the niosome and about 15 to 25 mg Fulvic acid dissolved in water in the outer layer. In other embodiments, the composition described herein comprises about 5 to 15 mg chloroform extract of mint (*Mentha arvensis* Linn), about 25 to 50 mg *Ginkgo biloba,* 15 to 25 mg kaempferol Iodine-127 (stable non-radioactive iodine isotope conjugated with Kaempferol), and about 50 to 150 mg calcium alginate in the inner layer of the niosome and about 50 to 150 mg sodium alginate and about 15 to 25 mg fulvic acid dissolved in water in the outer layer. Using niosome as the carrier of these compounds not only increases oral bioavailability but also facilitates the carrying of both hydrophobic and hydrophilic agents simultaneously.

In some embodiments, the present invention features a multi-layer niosome nanocarrier drug composition. The drug composition may comprise an inner layer comprising chloroform extract of mint and Kaempferol Iodine-127 and an outer layer comprising fulvic acid. In other embodiments, the drug composition may comprise an inner layer comprising chloroform extract of mint, Kaempferol Iodine-127, calcium alginate, and *Ginkgo biloba* extract, and an outer layer comprising fulvic acid and sodium alginate.

In other embodiments, the present invention features a method of preventing or treating radiation damage in a subject in need thereof. In some embodiments, the method comprises administering a multi-layer niosome nanocarrier drug composition as described herein. In some embodiments, the present invention features a method of removing radioactive material from a subject in need thereof, where the method comprises administering a multi-layer niosome nanocarrier drug composition as described herein.

The compositions and methods of present invention features encompass several unique and inventive technical features. Firstly, the compositions described herein feature a unique dual-action functionality, effectively chelating and removing radioactive elements such as I-131 and Sr90 from the body. Furthermore, it aids in the recovery from the detrimental effects of previously absorbed radioactive materials.

Secondly, Herbostroiodine is more effective than the currently available radioprotective drug, specifically potassium-iodine. The present invention achieves this by combining key components like Kaempferol, sodium alginate, calcium alginate, *Ginkgo biloba*, fulvic acid, and mint extract in specific concentrations. This unique blend provides the compositions described herein (i.e., drugs) with high radioprotective and antioxidant effects, activating various antioxidant and anti-inflammation mechanisms in the body.

Thirdly, this invention is notable for being the first radioprotective drug with minimal to almost no adverse side effects while maintaining a high therapeutic index.

Finally, the mechanism of action of Herbostroiodine draws inspiration from two of the most radioactivity-resistant creatures, cockroaches and bdelloid rotifers. By incorporating elements from these resilient organisms, the drug offers an innovative approach to radioactivity protection.

Moreover, the prior references teach away from the present invention. For example, the current radioprotective drug, potassium-iodine, causes thyroid cancer in the long term; when the thyroid absorbs radioactive iodine, it can increase the risk of thyroid cancer in infants, children, and young adults along with gastrointestinal problems, rashes, and inflammation of the salivary glands.

Furthermore, the inventive technical features of the present invention contribute to a surprising result. For example, the combination of fulvic acid with Kaempferol and sodium alginate can absorb Sr90 more efficiently than fulvic acid, calcium alginate, or Kaempferol alone.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE SEVERAL VIEWS OF THE DRAWING(S)

The features and advantages of the present invention will become apparent from a consideration of the following detailed description presented in connection with the accompanying drawings in which.

DETAILED DESCRIPTION OF THE INVENTION

Figure 1:
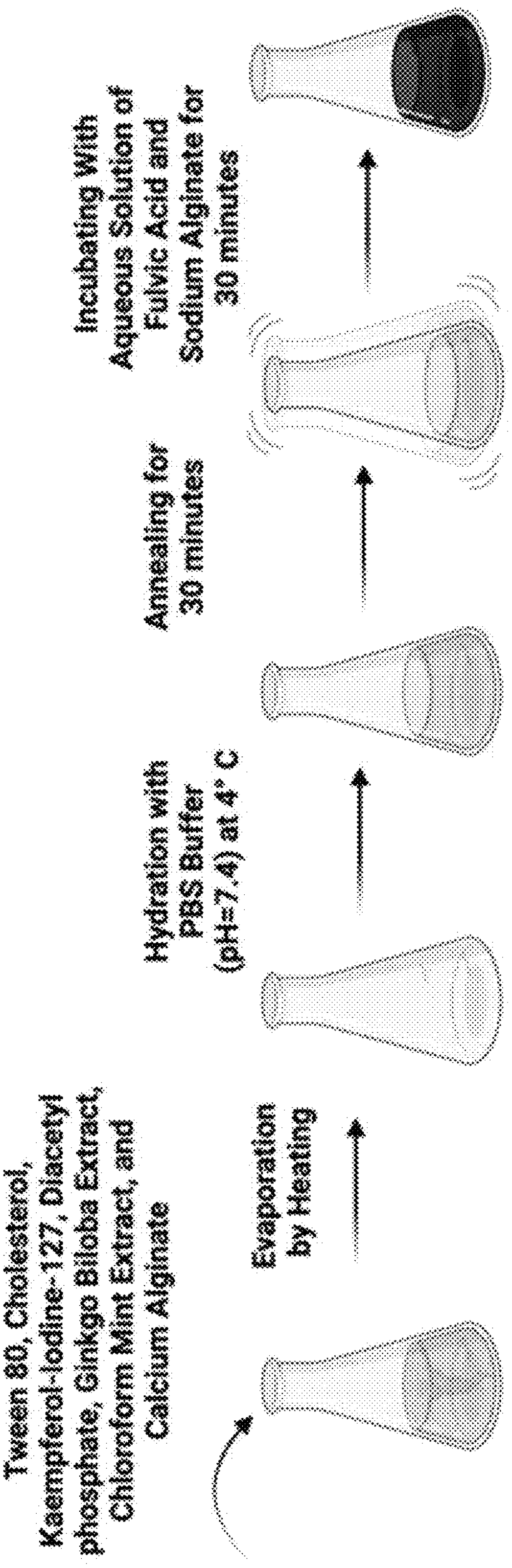
FIG. 1 shows a non-limiting example of a method for preparing the composition (e.g., drug) described herein.

Disclosed are the various compounds, solvents, solutions, carriers, and/or components to be used to prepare the compositions to be used within the methods disclosed herein. Also disclosed are the various steps, elements, amounts, routes of administration, symptoms, and/or treatments that are used or observed when performing the disclosed methods, as well as the methods themselves. These and other materials, steps, and/or elements are disclosed herein, and it is understood that when combinations, subsets, interactions, groups, etc. of these materials are disclosed, while specific reference of each various individual and collective combination and permutation of these compounds may not be explicitly disclosed, each is specifically contemplated and described herein.

Unless otherwise explained, all technical and scientific terms used herein have the same meaning as commonly understood by one of ordinary skill in the art to which a disclosed invention belongs. The singular terms "a," "an," and "the" include plural referents unless context clearly indicates otherwise. Similarly, the word "or" is intended to include "and" unless the context clearly indicates otherwise. The term "comprising" means that other elements can also be present in addition to the defined elements presented. The use of "comprising" indicates inclusion rather than limitation. Stated another way, the term "comprising" means "including principally, but not necessarily solely." Furthermore, variations of the word "comprising," such as "comprise" and "comprises," have correspondingly the same meanings. In one respect, the technology described herein related to the herein described compositions, methods, and respective component(s) thereof, as essential to the invention, yet open to the inclusion of unspecified elements, essential or not ("comprising").

Although methods and materials similar or equivalent to those described herein can be used to practice or test the disclosed technology, suitable methods and materials are described below. The materials, methods, and examples are illustrative only and not intended to be limiting.

A "subject" is an individual and includes, but is not limited to, a mammal (e.g., a human, horse, pig, rabbit, dog, sheep, goat, non-human primate, cow, cat, guinea pig, or rodent), a fish, a bird, a reptile or an amphibian. The term does not denote a particular age or sex. Thus, adult and newborn subjects, as well as fetuses, whether male or female, are intended to be included. A "patient" is a subject afflicted with a disease or disorder.

The terms "administering" and "administration" refer to methods of providing a pharmaceutical preparation, composition, or formulation to a subject. The compositions described herein can be administered in a number of ways depending on whether local or systemic treatment is desired and on the area to be treated. Such methods are well known to those skilled in the art and include, but are not limited to, administering the compositions orally, intranasally, parenterally (e.g., intravenously and subcutaneously), by intramuscular injection, by intraperitoneal injection, intrathecally, transdermally, extracorporeally, topically or the like.

Pharmaceutical peptide compositions for oral administration include but are not limited to, powders or granules, suspensions or solutions in water or non-aqueous media, pills, lozenges, capsules, sachets, or tablets. Thickeners, flavorings, diluents, emulsifiers, dispersing aids, or binders may be desirable. A person of skill, monitoring a subject's clinical response can adjust the frequency of administration and dosage of the medication according to methods known in the art.

Figure 2:
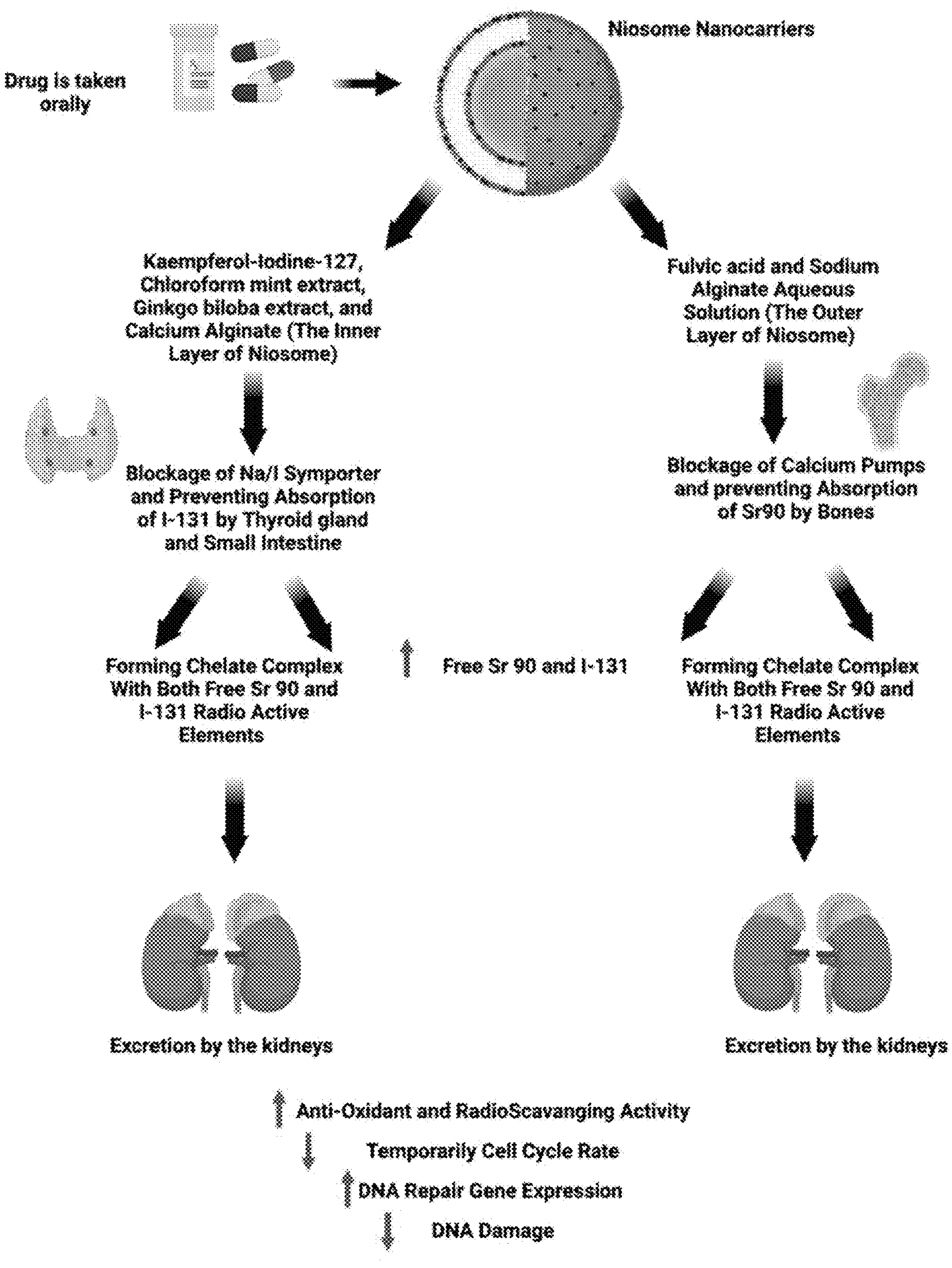
FIG. 2 shows non-limiting mechanisms of action (e.g., dual mechanism of action) for the compositions herein work.

Referring now to FIGS. 1 and 2, the present invention features compositions and methods of producing said compositions for radioprotection.

Compositions

The present invention features a multi-layer niosome nanocarrier drug composition, i.e., Herbostroiodine. In some embodiments, the multi-layer niosome nanocarrier drug composition comprises an herbal extract (e.g., extract of mint), an organic acid (e.g., fulvic acid or humic acid), and a flavonoid (e.g., Kaempferol Iodine-127). In some embodiments, the herbal extract and the flavonoid are within an inner layer of the niosome (e.g., the inner core of the niosome). In some embodiments, the organic acid is within an outer layer of the niosome. For example, in some embodiments, the drug composition comprises an extract of mint, Kaempferol Iodine-127 (stable non-radioactive iodine conjugated with Kaempferol), and fulvic acid. In some embodiments, the extract of mint and Kaempferol Iodine-127 (non-radioactive iodine conjugated with Kaempferol) are within an inner layer of the niosome (e.g., the inner core of the niosome). In some embodiments, the fulvic acid is within an outer layer of the niosome. In some embodiments, the niosome may further comprise *Ginkgo biloba* extract, calcium alginate, sodium alginate, or a combination thereof. For example, the extract of mint, Kaempferol Iodine-127, *Ginkgo biloba* extract, and calcium alginate are within an inner layer of the niosome (e.g., the inner core of the niosome). In some embodiments, the sodium alginate and fulvic acid are within an outer layer of the niosome.

Without wishing to limit the present invention to any theory of mechanism, it is believed that the multi-layer niosome nanocarrier drug compositions, further comprising *Ginkgo biloba* extract, calcium alginate, and sodium alginate, significantly enhance both the chelating activity and anticancer efficacy of the drug compositions described herein. Thus, in some embodiments, the drug composition comprises an extract of mint, Kaempferol Iodine-127 (stable non-radioactive iodine conjugated with kaempferol), *Ginkgo biloba* extract, calcium alginate, sodium alginate, and fulvic acid. In some embodiments, the extract of mint, Kaempferol Iodine-127, *Ginkgo biloba* extract, and calcium alginate are within an inner layer of the niosome (e.g., the inner core of the niosome). In some embodiments, the sodium alginate and fulvic acid are within an outer layer of the niosome.

In some embodiments, the composition comprises about 10 mg of mint extract (*Mentha arvensis* Linn). In some embodiments, the composition comprises about 1 mg of mint extract. In some embodiments, the composition comprises about 5 mg of mint extract. In some embodiments, the composition comprises about 15 mg of mint extract. In some embodiments, the composition comprises about 20 mg of mint extract. In some embodiments, the composition comprises about 25 mg of mint extract. In some embodiments, the composition comprises about 50 mg of mint extract. In some embodiments, the composition comprises about 5 to 50 mg of mint extract. In some embodiments, the composition comprises about 5 to 25 mg of mint extract. In some embodiments, the composition comprises about 5 to 20 mg of mint extract. In some embodiments, the composition comprises about 5 to 15 mg of mint extract.

As used herein, "extract of mint," "mint extract," and "chloroform extract of mint" may be used interchangeably. In some embodiments, the chloroform extract of mint is prepared by extracting mint leaves with a minimal amount of chloroform, which is fully evaporated during synthesis, leaving no chloroform residue in the final composition. Alternatively, other herbal extracts may be used without the need for any chloroform in the process.

In some embodiments, the composition comprises about 20 mg of Kaempferol Iodine-127 (non-radioactive iodine conjugated with Kaempferol). In some embodiments, the composition comprises about 10 mg of Kaempferol Iodine-127. In some embodiments, the composition comprises about 15 mg of Kaempferol Iodine-127. In some embodiments, the composition comprises about 25 mg of Kaempferol Iodine-127. In some embodiments, the composition comprises about 50 mg of Kaempferol Iodine-127. In some embodiments, the composition comprises about 75 mg of Kaempferol Iodine-127. In some embodiments, the composition comprises about 100 mg of Kaempferol Iodine-127. In some embodiments, the composition comprises about 200 mg of Kaempferol Iodine-127. In some embodiments, the composition comprises about 10 to 100 mg of Kaempferol Iodine-127. In some embodiments, the composition comprises about 10 to 75 mg of Kaempferol Iodine-127. In some embodiments, the composition comprises about 10 to 50 mg of Kaempferol Iodine-127. In some embodiments, the composition comprises about 10 to 25 mg of Kaempferol Iodine-127. In some embodiments, the composition comprises about 15 to 100 mg of Kaempferol Iodine-127. In some embodiments, the composition comprises about 15 to 75 mg of Kaempferol Iodine-127. In some embodiments, the composition comprises about 15 to 50 mg of Kaempferol Iodine-127. In some embodiments, the composition comprises about 15 to 25 mg of Kaempferol Iodine-127.

In some embodiments, the composition comprises 20 mg of fulvic acid. In some embodiments, the composition comprises about 1 mg of fulvic acid. In some embodiments, the composition comprises about 5 mg of fulvic acid. In some embodiments, the composition comprises about 10 mg of fulvic acid. In some embodiments, the composition comprises about 15 mg of fulvic acid. In some embodiments, the composition comprises about 25 mg of fulvic acid. In some embodiments, the composition comprises about 50 mg of fulvic acid. In some embodiments, the composition comprises about 10 to 50 mg of fulvic acid. In some embodiments, the composition comprises about 10 to 25 mg of fulvic acid. In some embodiments, the composition comprises about 10 to 15 mg of fulvic acid. In some embodiments, the composition comprises about 15 to 50 mg of fulvic acid. In some embodiments, the composition comprises about 15 to 25 mg of fulvic acid.

In some embodiments, the composition comprises 30 mg of *Ginkgo biloba*. In some embodiments, the composition comprises about 10 mg of *Ginkgo biloba*. In some embodiments, the composition comprises about 25 mg of *Ginkgo biloba*. In some embodiments, the composition comprises about 50 mg of *Ginkgo biloba*. In some embodiments, the composition comprises about 75 mg of *Ginkgo biloba*. In some embodiments, the composition comprises about 100 mg of *Ginkgo biloba*. In some embodiments, the composition comprises about 10 to 100 mg of *Ginkgo biloba*. In some embodiments, the composition comprises about 10 to 75 mg of *Ginkgo biloba*. In some embodiments, the composition comprises about 10 to 50 mg of *Ginkgo biloba*. In some embodiments, the composition comprises about 10 to 25 mg of *Ginkgo biloba*. In some embodiments, the composition comprises about 25 to 100 mg of *Ginkgo biloba*. In some embodiments, the composition comprises about 25 to 75 mg of *Ginkgo biloba*. In some embodiments, the composition comprises about 25 to 50 mg of *Ginkgo biloba*.

In some embodiments, the composition comprises 100 mg of calcium alginate. In some embodiments, the composition comprises about 10 mg of calcium alginate. In some embodiments, the composition comprises about 25 mg of calcium alginate. In some embodiments, the composition comprises about 50 mg of calcium alginate. In some embodiments, the composition comprises about 75 mg of calcium alginate. In some embodiments, the composition comprises about 150 mg of calcium alginate. In some embodiments, the composition comprises about 200 mg of calcium alginate. In some embodiments, the composition comprises about 25 to 200 mg of calcium alginate. In some embodiments, the composition comprises about 25 to 150 mg of calcium alginate. In some embodiments, the composition comprises about 25 to 100 mg of calcium alginate. In some embodiments, the composition comprises about 25 to 75 mg of calcium alginate. In some embodiments, the composition comprises about 50 to 200 mg of calcium alginate. In some embodiments, the composition comprises about 50 to 150 mg of calcium alginate. In some embodiments, the composition comprises about 50 to 100 mg of calcium alginate. In some embodiments, the composition comprises about 50 to 75 mg of calcium alginate.

In some embodiments, the composition comprises 100 mg of sodium alginate. In some embodiments, the composition comprises about 10 mg of sodium alginate. In some embodiments, the composition comprises about 25 mg of sodium alginate. In some embodiments, the composition comprises about 50 mg of sodium alginate. In some embodiments, the composition comprises about 75 mg of sodium alginate. In some embodiments, the composition comprises about 150 mg of sodium alginate. In some embodiments, the composition comprises about 200 mg of sodium alginate. In some embodiments, the composition comprises about 25 to 200 mg of sodium alginate. In some embodiments, the composition comprises about 25 to 150 mg of sodium alginate. In some embodiments, the composition comprises about 25 to 100 mg of sodium alginate. In some embodiments, the composition comprises about 25 to 75 mg of sodium alginate. In some embodiments, the composition comprises about 50 to 200 mg of sodium alginate. In some embodiments, the composition comprises about 50 to 150 mg of sodium alginate. In some embodiments, the composition comprises about 50 to 100 mg of sodium alginate. In some embodiments, the composition comprises about 50 to 75 mg of sodium alginate.

In some embodiments, the present invention features an herbal extended-release radio-protective drug formulated using a multi-layer niosome nanocarrier. In some embodiments, the composition described herein comprises about 5 mg to 15 mg extract of mint (*Mentha arvensis* Linn), about 15 mg to 25 mg Kaempferol Iodine-127 (non-radioactive iodine isotope conjugated with Kaempferol) in the inner layer of the niosome and about 15 mg to 25 mg fulvic acid dissolved in water in the outer layer of the niosome. In other embodiments, the composition described herein comprises 10 mg extract of Mint (*Mentha arvensis* Linn), 20 mg Kaempferol Iodine-127 (non-radioactive iodine isotope conjugated with Kaempferol) in the inner layer of the niosome and 20 mg fulvic acid dissolved in water in the outer layer of the niosome.

In some embodiments, the present invention features an herbal extended-release radio-protective drug formulated using a multi-layer niosome nanocarrier. In some embodiments, the composition described herein comprises about 5 mg to 15 mg extract of mint (*Mentha arvensis* Linn), about 15 mg to 25 mg Kaempferol Iodine-127 (stable non-radioactive iodine isotope conjugated with Kaempferol), 25 mg to 50 mg *Ginkgo biloba* extract, and about 50 mg to 150 mg calcium alginate in the inner layer of the niosome and about 15 mg to 25 mg fulvic acid and 50 mg to 150 mg sodium alginate together dissolved in water in the outer layer of the niosome. In other embodiments, the composition described herein comprises 10 mg chloroform extract of mint (*Mentha arvensis* Linn), 20 mg kaempferol Iodine-127 (stable non-radioactive iodine isotope conjugated with Kaempferol), 30 mg *Ginkgo biloba* extract, and 100 mg calcium alginate in the inner layer of the niosome and 20 mg fulvic acid and 100 mg sodium alginate together dissolved in water in the outer layer of the niosome.

The compositions described herein (e.g., Herbostroiodine) exhibit versatile applications, serving as 1) a potent radioprotective drug against I-131 and Sr90 exposure; 2) an anti-cancer drug, particularly geared towards bone and thyroid cancers; 3) a robust anti-inflammatory and antioxidant drug; and 4) viable alternatives to I-131 medications with adverse side effects commonly prescribed for thyroid cancer treatment.

The composition described herein (e.g., Herbostroiodine) may be administered orally, where it enters the bloodstream and gradually dispenses its active components. Specifically, the fulvic acid and/or sodium alginate found in the outer layer, form chelates with Sr90 and I-131, facilitating the elimination of the chelated radioactive elements through the kidneys. Additionally, the hydrophobic core of the niosomes contained within the formulation gradually releases compounds (which comprises a combination of chloroform extract of mint, *Ginkgo biloba*, calcium alginate, and Kaempferol-iodine127) that inhibit the absorption of I-131 by the thyroid glands and Sr90 by the bones and intestines. Beyond these actions, Herbostroiodine triggers various mechanisms that enhance the body's antioxidant capabilities and ability to scavenge reactive oxygen species (ROS) and radioactive materials.

The drug compositions of the present invention are not confined to the components mentioned above and may additionally include other compatible components in accordance with the present invention. For instance, other herbal extracts may replace the extract of mint, such as sunflower seed oil, *Allium sativum* (garlic), *Silybum marianum* (milk thistle), *Coriandrum sativum* (cilantro), *Ginkgo biloba* (*ginkgo*), *Curcuma longa* (turmeric), phytochelatins, Triphala, herbal fibers, and Chlorophyta (green algae). Similarly, alternative flavonoids with effects comparable to Kaempferol Iodine-127, such as quercetin, myricetin, fisetin, apigenin, and curcumin, may be used. For *Ginkgo biloba* extract, other herbal extracts with a similar structure and effect-particularly Moringa oleifera, apigenin, punicalagin, Kaempferol 7-O-glucoside, quercetin, and epigallocatechin gallate—are also effective, with Moringa oleifera and *Ginkgo biloba* showing the strongest efficacy. Other alginates may be used to replace either calcium alginate or sodium alginate. For example, alkaline earth metals such as magnesium may substitute for calcium, while alkali metals such as potassium may replace sodium. Lastly, humic acid may be substituted for fulvic acid.

Methods of Preparing

According to some embodiments, the present invention may further comprise a method of preparing a multi-layer niosome nanocarrier drug composition. In some embodiments, the method may comprise dissolving Kaempferol Iodine-127, mint extract, cholesterol, Tween 80, and diacetyl phosphate in chloroform followed by evaporation (e.g., by heat) to make the niosomes comprising Kaempferol-iodine127 and mint extract and incubating the formed niosome in fulvic acid aqueous solution for a period of time. Alternatively, in some embodiments, the method comprises dissolving Kaempferol Iodine-127, mint extract, cholesterol, diacetyl phosphate, and Tween 80 in chloroform and incubating this composition with fulvic acid aqueous solution for a period of time, followed by evaporating them with heating and adding deionized water to the dried formed compound.

In other embodiments, the method may comprise dissolving Kaempferol Iodine-127, mint extract, *Ginkgo biloba* extract, calcium alginate, cholesterol, Tween 80, and diacetyl phosphate in chloroform followed by evaporation (e.g., by heat) to make the niosomes comprising kaempferol-iodine127, mint extract, *Ginkgo biloba* extract, and calcium alginate and incubating the formed niosome in an aqueous solution containing fulvic acid and sodium alginate for a period of time. Alternatively, in some embodiments, the method comprises dissolving Kaempferol Iodine-127, mint extract, *Ginkgo biloba* extract, calcium alginate, cholesterol, diacetyl phosphate, and tween 80 in chloroform and incubating this composition with an aqueous solution containing fulvic acid and sodium alginate for a period of time, followed by evaporating them with heating and adding deionized water to the dried formed compound.

In some embodiments, the prepared niosomes (e.g., niosomes that are loaded with Kaempferol Iodine-127, mint extract, *Ginkgo biloba* extract, calcium alginate, or a combination thereof) are incubated in an aqueous solution containing fulvic acid and/or sodium alginate for about 30 minutes. In some embodiments, the prepared niosomes are incubated in an aqueous solution containing fulvic acid and/or sodium alginate for about 20 minutes. In some embodiments, the prepared niosomes are incubated in an aqueous solution containing fulvic acid and/or sodium alginate for about 10 minutes. In some embodiments, the prepared niosomes are incubated in an aqueous solution containing fulvic acid and/or sodium alginate for about 40 minutes. In some embodiments, the prepared niosomes are incubated in an aqueous solution containing fulvic acid and/or sodium alginate for about 60 minutes. In some embodiments, the prepared niosomes (e.g., niosomes that are loaded with Kaempferol Iodine-127, mint extract, *Ginkgo biloba* extract, calcium alginate, or a combination thereof) are incubated in an aqueous solution containing fulvic acid and/or sodium alginate for about 10 to 60 minutes, or about 10 to 40 minutes, or about 10 to 30 minutes, or about 10 to 20 minutes, or about 15 to 60 minutes, or about 15 to 40 minutes, or about 15 to 30 minutes, about 20 to 60 minutes, or about 20 to 40 minutes, or about 10 to 30 minutes.

In some embodiments, the prepared niosomes (e.g., niosomes that are loaded with Kaempferol Iodine-127, mint extract, *Ginkgo biloba* extract, calcium alginate, or a combination thereof) are incubated in about 1 mg/ml of an aqueous solution containing fulvic acid and/or sodium alginate. In some embodiments, the prepared niosomes are incubated in about 0.5 mg/ml of an aqueous solution containing fulvic acid and/or sodium alginate. In some embodiments, the prepared niosomes are incubated in about 0.1 mg/mL of an aqueous solution containing fulvic acid and/or sodium alginate. In some embodiments, the prepared niosomes are incubated in about 2 mg/ml of an aqueous solution containing fulvic acid and/or sodium alginate. In some embodiments, the prepared niosomes are incubated in about 5 mg/ml of an aqueous solution containing fulvic acid and/or sodium alginate. In some embodiments, the prepared niosomes are incubated in about 10 mg/ml of an aqueous solution containing fulvic acid and/or sodium alginate. In some embodiments, the prepared niosomes are incubated in about 0.1 to 10 mg/ml of an aqueous solution containing fulvic acid and/or sodium alginate. In some embodiments, the prepared niosomes are incubated in about 0.1 to 5 mg/ml of an aqueous solution containing fulvic acid and/or sodium alginate. In some embodiments, the prepared niosomes are incubated in about 0.1 to 1 mg/ml of an aqueous solution containing fulvic acid and/or sodium alginate. In some embodiments, the prepared niosomes are incubated in about 0.5 to 10 mg/ml of an aqueous solution containing fulvic acid and/or sodium alginate. In some embodiments, the prepared niosomes are incubated in about 0.5 to 5 mg/ml of an aqueous solution containing fulvic acid and/or sodium alginate. In some embodiments, the prepared niosomes are incubated in about 0.5 to 1 mg/mL of an aqueous solution containing fulvic acid and/or sodium alginate.

As used herein, a "prepared niosome" refers to the formed inner core of the niosome comprising Kaempferol Iodine-127, mint extract, *Ginkgo biloba* extract, calcium alginate, or a combination thereof. As used herein, a "loaded niosome" refers to a multi-layer noisome comprising an inner core and an outer layer; the loaded niosome may comprise Kaempferol Iodine-127, chloroform mint extract, *Ginkgo biloba* extract, calcium alginate, sodium alginate, fulvic acid, or a combination thereof.

In some embodiments, the methods may further comprise storing the loaded niosomes (e.g., niosomes loaded with Kaempferol Iodine-127, chloroform mint extract, *Ginkgo biloba* extract, calcium alginate, sodium alginate, fulvic acid, or a combination thereof) in an aqueous solution.

Methods of Use

The present invention may feature a method of preventing or treating radiation damage in a subject in need thereof. In some embodiments, the method comprises administering a multi-layer niosome nanocarrier drug composition as described herein. For example, the multi-layer niosome nanocarrier drug composition may comprise an inner layer comprising an extract of mint and Kaempferol Iodine-127 and an outer layer comprising fulvic acid. Alternatively, in some embodiments, the multi-layer niosome nanocarrier drug composition may comprise an inner layer comprising an extract of mint, Kaempferol Iodine-127*, Ginkgo biloba* extract, and calcium alginate, and an outer layer comprising fulvic acid and sodium alginate.

The present invention may also feature a method of removing radioactive material from a subject in need thereof. In some embodiments, the method comprises administering a multi-layer niosome nanocarrier drug composition as described herein. For example, the multi-layer niosome nanocarrier drug composition may comprise an inner layer comprising an extract of mint and Kaempferol Iodine-127 and an outer layer comprising fulvic acid. Alternatively, in some embodiments, the multi-layer niosome nanocarrier drug composition may comprise an inner layer comprising an extract of mint, Kaempferol Iodine-127*, Ginkgo biloba* extract, and calcium alginate, and an outer layer comprising fulvic acid and sodium alginate.

Dual Mechanism of Action:

Radioactive absorption blocking and chelating: Sr90 has biochemical behavior similar to calcium and is readily incorporated into bones and teeth, leading to bone cancer, and I-131 radioactive iodine) is absorbed by thyroid glands via transporters called Na/I symporters. This drug has fulvic acid aqueous solution in the outer layer (hydrophilic layer) that, upon interacting with cancer/radioactivates cells (in thyroid glands and bones), is released slowly, and then fulvic acid interacts radioactive elements like Sr90 by their phenol rings and form chelate with the Sr90 present in the cell and removes it through the kidneys. Meanwhile, the inner hydrophobic part of the drug with Kaempferol-Iodine127 and chloroform mint extract is released. The Kaempferol-Iodine 127 interacts with the Na/I symporters in thyroid glands with higher affinity than radioactive I-131 and, therefore, would be able to block the I-131 absorption by the thyroid glands and prevent thyroid cancer. The unabsorbed and free radioactive I-131 would then be chelated and removed with mint extract and Fulvic acid through the kidneys.

Other mechanisms that lead to an overall increase in antioxidant system and DNA repair: Apart from this, the drug induces its anti-cancer and radioprotective effects by various other mechanisms that are also seen in the most radioactive-resistant creatures in the universe, i.e., cockroaches and, including boosting body's antioxidant and ROS/radioactive scavenging activity, temporarily slowing down the cell cycle rate, reducing and preventing DNA damage, oxidative stress, and lipid peroxidation, upregulation of mRNA of antioxidant enzymes (such as catalase, glutathione-s-transferase, glutathione peroxidase, and superoxide dismutase), upregulation of DNA repair genes, inhibiting activation of protein kinase C, mitogen-activated protein kinase, cytochrome P-450, nitric oxide and several other genes that may be responsible for inducing damage following irradiation. These mechanisms have been shown in FIG. 2.

Example 1

The following is a non-limiting example of the present invention. It is to be understood that said example is not intended to limit the present invention in any way. Equivalents or substitutes are within the scope of the present invention.

Preparation method: Multilamellar vesicles (MLV) are prepared using a technique based on a gel hydration method (FIG. 1). Tween 80, cholesterol, and diacetyl phosphate in a molar ratio of (10:10:1) are weighed and dissolved in a chloroform/methanol system (2:1) in a 100 ml round bottom flask. The solvent mixture is evaporated to obtain a thin, dry film. The film is hydrated with 2 ml of PBS pH 7.4 at 4° C. with gentle shaking, during which MLVs are formed. The vesicles are allowed to anneal for 30 minutes. 100 μM of Kaempferol-Iodine127 (Kaempferol had already been mixed with iodine 127-1:1 ratio) and 100 μM chloroform mint extract is dissolved in chloroform along with cholesterol and Tween 80, and niosomes are prepared as mentioned earlier. Fulvic acid aqueous solution loading was performed by incubating Kaempferol-iodine-loaded niosomes in 1 mg/mL of fulvic acid solution for 30 minutes. Due to the hydrophilic nature of fulvic acid, it preferentially accumulates in the outer aqueous layer of the niosomes. The excess drug present in the supernatant is removed by washing with water. After preparation, the triple drug (Kaempferol-Iodine, chloroform mint extract, and fulvic acid) loaded niosome aqueous suspension was stored in the dark at 4° C. and later used for experiments.

Example 2

The following is a non-limiting example of the present invention. It is to be understood that said example is not intended to limit the present invention in any way. Equivalents or substitutes are within the scope of the present invention.

Preparation method: Multilamellar niosome vesicles (MLNV) are prepared as shown in FIG. 1. To prepare, tween 80, cholesterol, and diacetyl phosphate in a molar ratio of (10:10:1) are weighed and dissolved in a chloroform/methanol system (2:1) in a 100 ml round bottom flask. Kaempferol Iodine-127 (100 μM) (kaempferol had already been mixed with iodine 127-1:1 ratio) and chloroform mint extract (100 μM), *Ginkgo biloba* extract (100 μM), and calcium alginate (10 mM) are dissolved in chloroform along with cholesterol and tween 80. The solvent mixture is evaporated to obtain a thin, dry film. The film is hydrated with 2 ml of PBS pH 7.4 at 4° C. with gentle shaking, during which MLNVs are formed. The MLNVs are then allowed to anneal for 30 minutes. The preparation of the outer layer of the niosome, i.e., fulvic acid and sodium alginate aqueous solution is performed by incubating the prepared MLNVs (containing Kaempferol Iodine-127, calcium alginate, mint extract, and *Ginkgo biloba* extract) in 2 mg/ml of an aqueous solution containing fulvic acid and sodium alginate (1 mg fulvic acid+1 mg sodium alginate in 2 ml of water) for 30 minutes. The final aqueous niosome suspension containing mixtures of Kaempferol Iodine-127, mint extract, *Ginkgo biloba* extract, calcium alginate, sodium alginate, and fulvic acid, can be stored in the dark at 4° C.

Example 3

The following is a non-limiting example of the present invention. It is to be understood that said example is not intended to limit the present invention in any way. Equivalents or substitutes are within the scope of the present invention.

A woman recently diagnosed with cancer begins radiation therapy and is instructed to take an oral dose of a radioprotective drug (e.g., Herbostroiodine) before each session to reduce the harmful effects on healthy tissue. The drug helps protect against radiation-induced side effects, such as inflammation and tissue damage, allowing the therapy to focus on the cancer cells. After completing her treatment, she discontinues the drug. She experiences no side effects from the medication, and the typical radiation-related side effects are notably reduced, improving her overall comfort during therapy.

EMBODIMENTS

The following is a non-limiting example of the present invention. It is to be understood that said example is not intended to limit the present invention in any way. Equivalents or substitutes are within the scope of the present invention.

Embodiment 1: A multi-layer niosome nanocarrier drug composition comprising: a) an inner layer comprising an extract of mint and Kaempferol Iodine-127; and b) an outer layer comprising fulvic acid. Embodiment 2: The composition of embodiment 1, wherein the inner layer further comprises *Ginkgo biloba* extract. Embodiment 3: The composition of embodiment 1 or embodiment 2, wherein the inner layer further comprises calcium alginate. Embodiment 4: The composition of any one of embodiments 1-3, wherein the outer layer further comprises sodium alginate.

Embodiment 5: A multi-layer niosome nanocarrier drug composition comprising: a) an inner layer comprising an extract of mint, Kaempferol Iodine-127, *Ginkgo biloba* extract, and calcium alginate; and b) an outer layer comprising fulvic acid and sodium alginate.

Embodiment 6: The composition of any one of embodiments 1-5, wherein the composition comprises about 5 mg to 15 mg of the extract of mint. Embodiment 7: The composition of embodiment 6, wherein the composition comprises about 10 mg of the extract of mint.

Embodiment 8: The composition of any one of embodiments 1-7, wherein the composition comprises about 25 mg to 50 mg of *Ginkgo biloba* extract. Embodiment 9: The composition of embodiment 8, wherein the composition comprises about 30 mg of *Ginkgo biloba* extract.

Embodiment 10: The composition of any one of embodiments 1-9, wherein the composition comprises about 15 mg to 25 mg of the Kaempferol Iodine-127. Embodiment 11: The composition of embodiment 10, wherein the composition comprises about 20 mg of the Kaempferol Iodine-127.

Embodiment 12: The composition of any one of embodiments 1-10, wherein the composition comprises about 50 mg to 150 mg calcium alginate. Embodiment 13: The composition of embodiment 12, wherein the composition comprises about 100 mg of calcium alginate.

Embodiment 14: The composition of any one of embodiments 1-13, wherein the composition comprises about 15 mg to 25 mg of fulvic acid. Embodiment 15: The composition of embodiment 14, wherein the composition comprises about 20 mg of fulvic acid.

Embodiment 16: The composition of any one of embodiments 1-15, wherein the composition comprises about 50 mg to 150 mg of sodium alginate. Embodiment 17: The composition of embodiment 16, wherein the composition comprises about 100 mg of sodium alginate.

Embodiment 18: A multi-layer noisome nanocarrier drug composition comprising: a) an inner layer of the noisome comprising: i) about 5 mg to 15 mg extract of mint and ii) about 15 mg to 25 mg Kaempferol Iodine-127; and b) an outer layer of the noisome comprising about 15 to 25 mg fulvic acid. Embodiment 19: The composition of embodiment 18, wherein the inner layer further comprises about 25 mg to 50 mg *Ginkgo biloba* extract. Embodiment 20: The composition of embodiment 18 or embodiment 19, wherein the inner layer further comprises about 50 mg to 150 mg calcium alginate. Embodiment 21: The composition of any one of embodiments 18-21, wherein the outer layer further comprises about 50 mg to 150 mg sodium alginate.

Embodiment 22: A multi-layer niosome nanocarrier drug composition comprising: a) an inner layer comprising: i) about 5 mg to 15 mg extract of mint; ii) about 15 mg to 25 mg Kaempferol Iodine-127; iii) about 25 mg to 50 mg *Ginkgo biloba* extract, and iv) about 50 mg to 150 mg calcium alginate; and b) an outer layer comprising: i) about 15 mg to 25 mg fulvic acid, and ii) about 50 mg to 150 mg sodium alginate.

Embodiment 23: A method of preventing or treating radiation damage in a subject in need thereof, the method comprising administering a composition according to any one of embodiments 1-22. Embodiment 24: A method of removing radioactive material from a subject in need thereof, the method comprising administering a composition according to any one of embodiments 1-22.

Embodiment 25: A method of preventing or treating radiation damage in a subject in need thereof, the method comprising administering a multi-layer niosome nanocarrier drug composition comprising: a) an inner layer comprising an extract of mint and Kaempferol Iodine-127; and b) an outer layer comprising fulvic acid. Embodiment 26: A method of removing radioactive material from a subject in need thereof, the method comprising administering a multi-layer niosome nanocarrier drug composition comprising: a) an inner layer comprising an extract of mint and Kaempferol Iodine-127 and b) an outer layer comprising fulvic acid.

Embodiment 27: The method of embodiment 25 or embodiment 26, wherein the inner layer further comprises *Ginkgo biloba* extract. Embodiment 28: The method of any one of embodiments 25-27, wherein the inner layer further comprises calcium alginate. Embodiment 29: The method of any one of embodiments 25-28, wherein the outer layer further comprises sodium alginate.

Embodiment 30: The method of any one of embodiments 25-29, wherein the composition comprises about 5 mg to 15 mg of the extract of mint. Embodiment 31: The method of embodiment 30, wherein the composition comprises about 10 mg of the extract of mint.

Embodiment 32: The method of any one of embodiments 25-31, wherein the composition comprises about 25 mg to 50 mg of *Ginkgo biloba* extract. Embodiment 33: The method of embodiment 32, wherein the composition comprises about 30 mg of *Ginkgo biloba* extract.

Embodiment 34: The method of any one of embodiments 25-33, wherein the composition comprises about 15 mg to 25 mg of the Kaempferol Iodine-127.

Embodiment 35: The method of embodiment 34, wherein the composition comprises about 20 mg of the Kaempferol Iodine-127.

Embodiment 36: The method of any one of embodiments 25-35, wherein the composition comprises about 50 mg to 150 mg calcium alginate. Embodiment 37: The method of embodiment 36, wherein the composition comprises about 100 mg of calcium alginate.

Embodiment 38: The method of any one of embodiments 25-37, wherein the composition comprises about 15 mg to 25 mg of fulvic acid. Embodiment 39: The method of embodiment 38, wherein the composition comprises about 20 mg of fulvic acid.

Embodiment 40: The method of any one of embodiments 25-39, wherein the composition comprises about 50 mg to 150 mg of sodium alginate. Embodiment 41: The method of embodiment 40, wherein the composition comprises about 100 mg of sodium alginate.

Embodiment 42: A method of preparing a multi-layer niosome nanocarrier drug composition, the method comprising: a) dissolving a first mixture comprising Kaempferol Iodine-127 and chloroform mint extract in chloroform to produce a second mixture; b) evaporating the second mixture to make niosomes comprising Kaempferol Iodine-127 and mint extract, and c) incubating the niosomes in an incubation solution comprising fulvic acid for a period of time. Embodiment 43: The method of embodiment 42, wherein the first mixture further comprises *Ginkgo biloba* extract and calcium alginate. Embodiment 44: The method of embodiment 42 or embodiment 43, wherein the incubation solution further comprises sodium alginate.

Embodiment 45: A method of preparing a multi-layer niosome nanocarrier drug composition, the method comprising: a) dissolving a first mixture comprising Kaempferol-Iodine 127, chloroform mint extract, *Ginkgo biloba* extract, and calcium alginate in chloroform to produce a second mixture; b) evaporating the second mixture to make niosomes comprising Kaempferol-Iodine 127, chloroform mint extract, *Ginkgo biloba* extract, and calcium alginate, and c) incubating the niosomes in an incubation solution comprising fulvic acid and sodium alginate for a period of time.

Embodiment 46: The method of any one of embodiments 42-45, wherein the first mixture further comprises cholesterol, Tween 80, diacetyl phosphate, or a combination thereof. Embodiment 47: The method of any one of embodiments 42-46, wherein the evaporation is done by heating. Embodiment 48: The method of any one of embodiments 42-47, wherein the niosomes are incubated for 30 minutes. Embodiment 49: The method of any one of embodiments 42-48 further comprising storing the niosomes in an aqueous solution.

As used herein, the term "about" refers to plus or minus 10% of the referenced number.

Although there has been shown and described the preferred embodiment of the present invention, it will be readily apparent to those skilled in the art that modifications may be made thereto that do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only, and the claims are not limited by the dimensions of the figures. In some embodiments, descriptions of the inventions described herein using the phrase "comprising" include embodiments that could be described as "consisting essentially of" or "consisting of," and as such, the written description requirement for claiming one or more embodiments of the present invention using the phrase "consisting essentially of" or "consisting of" is met.

What is claimed is:

1. A multi-layer niosome nanocarrier drug composition comprising:

a) an inner layer comprising an extract of mint and Kaempferol Iodine-127; and b) an outer layer comprising fulvic acid.

2. The composition of claim 1, wherein the inner layer further comprises one or a combination of *Ginkgo biloba* extract or calcium alginate.

3. The composition of claim 1, wherein the outer layer further comprises sodium alginate.

4. The composition of claim 1, wherein the composition comprises about 5 mg to 15 mg of the extract of mint.

5. The composition of claim 1, wherein the composition comprises about 15 mg to 25 mg of the Kaempferol Iodine-127.

6. The composition of claim 1, wherein the composition comprises about 15 mg to 25 mg of fulvic acid.

7. The composition of claim 2, wherein the composition comprises about 25 mg to 50 mg of *Ginkgo biloba* extract.

8. The composition of claim 2, wherein the composition comprises about 50 mg to 150 mg calcium alginate.

9. The composition of claim 3, wherein the composition comprises about 50 mg to 150 mg of sodium alginate.

10. A method of preventing or treating radiation damage in a subject in need thereof, the method comprising administering the multi-layer niosome nanocarrier drug composition according to claim 1.

11. A method of removing radioactive material from a subject in need thereof, the method comprising administering the multi-layer niosome nanocarrier drug composition according to claim 1.

12. A multi-layer niosome nanocarrier drug composition comprising:

a) an inner layer comprising extract of mint, Kaempferol Iodine-127*, Ginkgo biloba* extract, and calcium alginate, and b) an outer layer comprising fulvic acid and sodium alginate.

13. A method of preventing or treating radiation damage in a subject in need thereof, the method comprising administering a multi-layer niosome nanocarrier drug composition comprising:

a) an inner layer comprising an extract of mint and Kaempferol Iodine-127; and b) an outer layer comprising fulvic acid.

14. The method of claim 13, wherein the inner layer further comprises one or a combination of *Ginkgo biloba* extract or calcium alginate, and wherein the outer layer further comprises sodium alginate.

15. The method of claim 13, wherein the composition comprises about 5 mg to 15 mg of the extract of mint.

16. The method of claim 13, wherein the composition comprises about 15 mg to 25 mg of the Kaempferol Iodine-127.

17. The method of claim 13, wherein the composition comprises about 15 mg to 25 mg of fulvic acid.

18. The method of claim 14, wherein the composition comprises about 25 mg to 50 mg of *Ginkgo biloba* extract.

19. The method of claim 14, wherein the composition comprises about 50 mg to 150 mg calcium alginate.

20. The method of claim 14, wherein the composition comprises about 50 mg to 150 mg of sodium alginate.

* * * * *